United States Patent [19]

Takano

[11] 4,454,882
[45] Jun. 19, 1984

[54] LASER APPARATUS UTILIZING MARKING LASER FOR TRIGGERING OPERATIVE LASER

[75] Inventor: Akira Takano, Tokyo, Japan

[73] Assignee: Olympus Optical Co., Ltd., Tokyo, Japan

[21] Appl. No.: 399,811

[22] Filed: Jul. 19, 1982

[30] Foreign Application Priority Data

Jul. 29, 1981 [JP] Japan ............................. 56-118681

[51] Int. Cl.³ ............................................... A61N 3/00
[52] U.S. Cl. ........................................ 128/395; 128/6;
128/303.1; 219/121 LZ; 372/14
[58] Field of Search .................... 128/4, 6, 303.1, 395;
219/121 L, 121 LS, 121 LU, 121 LZ, 121 LM;
250/233; 372/9, 14

[56] References Cited

U.S. PATENT DOCUMENTS

| | | | |
|---|---|---|---|
| 3,525,332 | 8/1970 | Kosaka | 128/6 |
| 3,533,707 | 10/1970 | Weiss | 128/303.1 |
| 3,710,798 | 1/1973 | Bredemeier | 128/395 |
| 4,309,998 | 1/1982 | Aror nee Rosa et al. | 128/303.1 |
| 4,316,467 | 2/1982 | Muckerheide | 128/303.1 |
| 4,336,809 | 6/1982 | Clark | 128/303.1 |

FOREIGN PATENT DOCUMENTS 55-77989  6/1980  Japan ............................. 291/121 LZ Primary Examiner—William E. Kamm
Assistant Examiner—Mitchell J. Shein

[57] ABSTRACT

A laser apparatus includes an operating laser oscillator for generating an operating laser beam for medical treatment and a marker laser oscillator for generating a visible laser beam (i.e., marker laser beam) in order to mark a portion of the body cavity to be treated. The marker laser beam is guided coaxial with the operating laser beam to become incident on a laser probe. The marker laser beam is intermittently shielded by a chopper. The shielded marker laser beam is reflected by a reflecting surface of the chopper and is guided to a photosensor. The operating laser oscillator is driven in response to an output signal from the photosensor.

9 Claims, 8 Drawing Figures

LASER APPARATUS UTILIZING MARKING LASER FOR TRIGGERING OPERATIVE LASER

BACKGROUND OF THE INVENTION

The present invention relates to a laser apparatus and, more particularly, to a laser apparatus used together with an endoscope.

Endoscopic laser apparatuses used together with endoscopes have been developed and are commercially available. According to an endoscopic laser apparatus of this type, a YAG laser oscillator is used to generate an operating laser beam. However, since the YAG laser beam is an invisible light ray, the operator cannot confirm the portion of the body cavity on which the beam is radiated. Undesired portions of the body cavity may therefore be radiated with the operating laser beam. In order to prevent this problem, a visible He-Ne laser beam as a marker laser beam is radiated together with the YAG laser beam as the operating laser beam to perform treatment while confirming the radiated portion of the body cavity with the marker laser beam. However, since the He-Ne laser beam is conventionally radiated continuously on the portion, the color (red) of the He-Ne laser beam cannot be discriminated from that of the radiated portion e.g. the walls of a stomach, so that the operator can hardly confirm the marker beam.

Further, in order to determine whether or not the operating laser beam is emitted, the marker laser beam is conventionally split into two beams by a beam splitter. One marker laser beam is used to confirm radiation of the operating laser beam, while the other marker laser beam is guided to the portion to be treated. Therefore, the amount of the other marker laser beam guided to the portion is small. As a result, it is difficult for the operator to confirm the radiated portion with the marker laser beam.

SUMMARY OF THE INVENTION

It is, therefore, an object of the present invention to provide a laser apparatus with which the operator can easily confirm a portion of a body cavity radiated with an operating laser beam, and which does not allow accidental radiation of the operating laser beam on any portion of the body cavity.

In order to achieve the above object of the present invention, there is provided a laser apparatus wherein a chopper is arranged in an optical path of a marker laser beam to alternately perform transmission and reflection of the marker laser beam a marker laser beam reflected by the chopper is detected by a photosensor, and an operating laser beam is generated by an operating laser oscillator in response to an output from the photosensor.

DETAILED DESCRIPTION OF THE PREFERRED EMBODIMENTS

Figure 1:
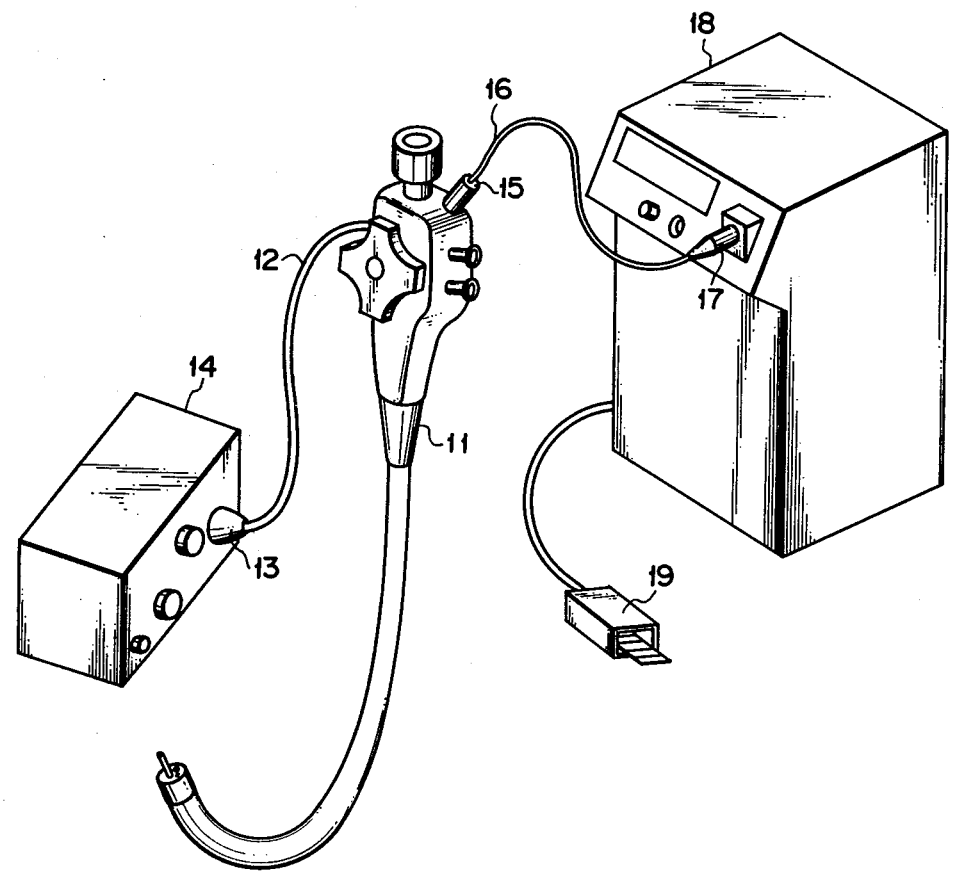
FIG. 1 is a perspective view of an endoscope system using a laser apparatus according to one embodiment of the present invention.

According to the endoscope system shown in FIG. 1, a connector 13 mounted at the distal end of a universal cord 12 of an endoscope 11 is connected to a light supply unit 14. A laser probe 16 is inserted into a forceps channel from a forceps channel inlet 15 of the endoscope 11. A connector 17 of the laser probe 16 is coupled to a laser apparatus 18.

Figure 2:
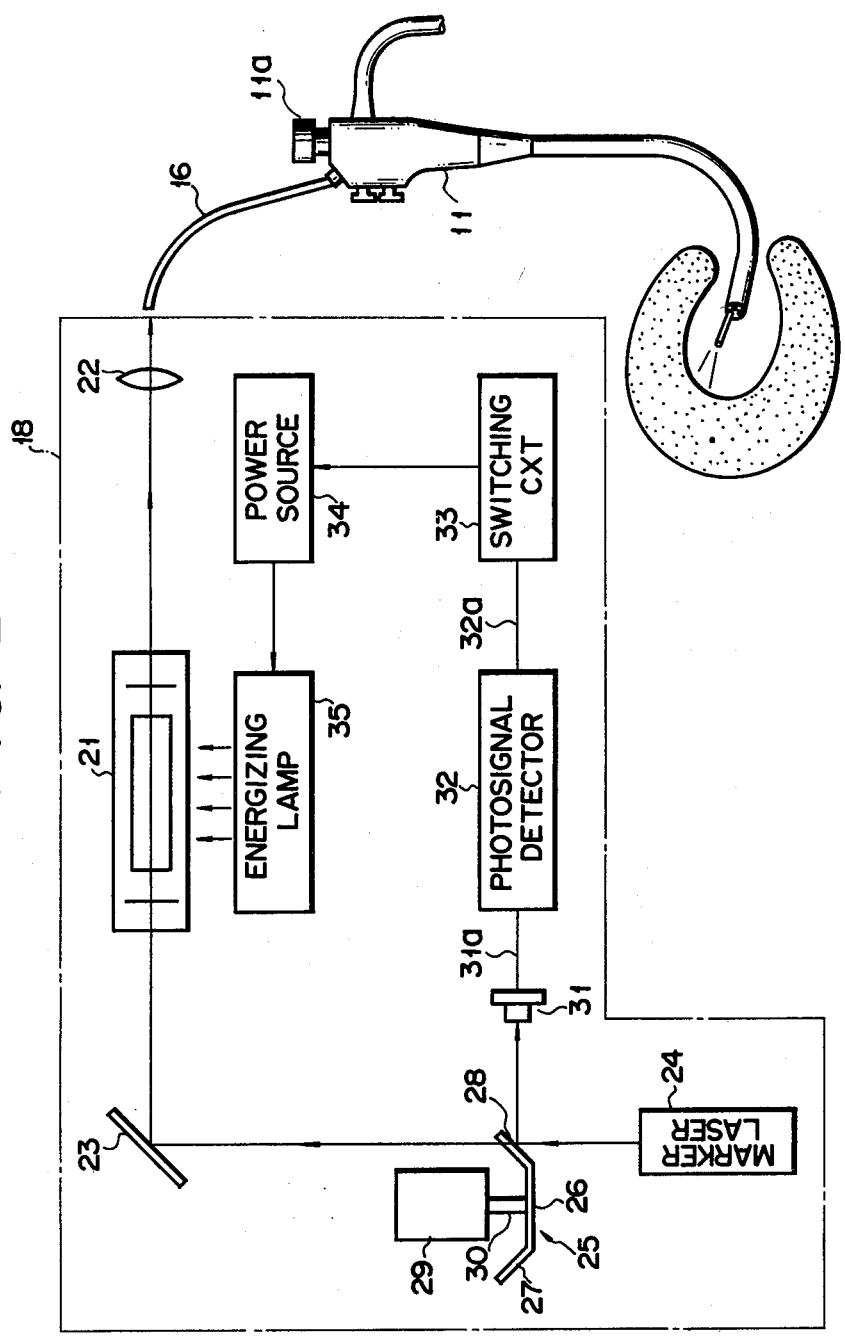
FIG. 2 is a schematic view of the endoscope system including a block diagram of the laser apparatus shown in FIG. 1.
Figure 3:
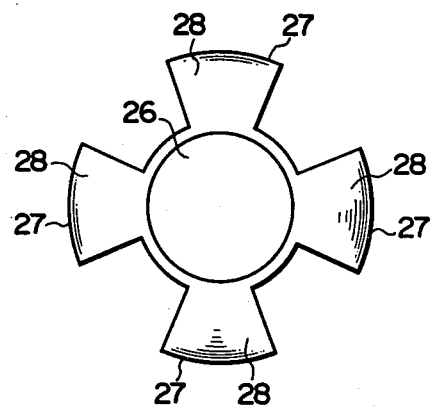
FIG. 3 is a plan view of a chopper shown in FIG. 2.
Figure 4:
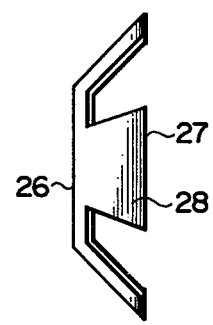
FIG. 4 is a sectional view of the chopper shown in FIG. 3.

An operating laser oscillator 21 such as a YAG laser oscillator is arranged in the laser apparatus 18, as shown in FIG. 2. A focusing lens 22 is arranged on the optical axis and at the output side of the operating laser oscillator 21. The focusing lens 22 focuses the laser beam on the laser probe 16. A reflecting mirror 23 is disposed on the optical axis as tilted at, for example, 45° with respect thereto and is located at the side of the operating laser oscillator 21 opposite to the output side described above. A marker laser oscillator 24 such as a helium-neon (He-Ne) laser oscillator is arranged perpendicular to the optical axis of the operating laser oscillator 21 and opposes the reflecting mirror 23. A chopper 25 is interposed between the reflecting mirror 23 and the marker laser oscillator 24. The chopper 25 which is a substantially truncated conical rotary body has a base plate 26 and reflecting plates 27, as shown in FIGS. 3 and 4. The reflecting plates comprise vanes which are integrally formed at equal intervals on the periphery of the base plate 26 and which extend therefrom at, for example, 45°. A reflecting surface 28 is formed on the outer surface of each reflecting plate 27. A rotating shaft 30 of a motor 29 which is parallel to the optical axis of the marker laser oscillator 24 is rotatably mounted at the center of the base plate 26.

A photosensor 31 opposes the reflecting surface 28 of the chopper 25 and is perpendicular to the optical axis of the marker laser oscillator 24. The output terminal of the photosensor 31 is connected to the input terminal of a photosignal detector 32. The photosignal detector 32 comprises an integrator circuit for integrating an output from the photosensor 31. The output terminal of the photosignal detector 32 is connected to the control input terminal of a switching circuit 33. The control output terminal of the switching circuit 33 is connected to the on-off terminal of a power source 34. The output terminal of the power source 34 is connected to an energizing lamp 35 arranged in the vicinity of the operating laser oscillator 21.

Figure 5:
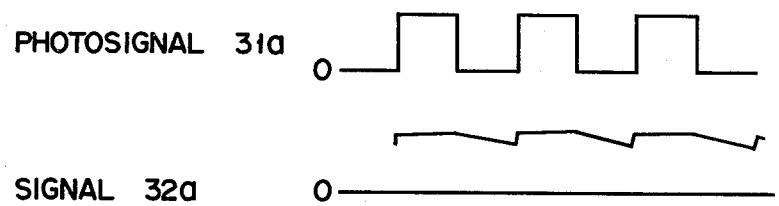
FIG. 5 is a timing chart of signals appearing in the circuit of the laser apparatus in FIG. 2.

The mode of operation of the laser apparatus with the above arrangement will be described. When the operator turns on a power switch of the light supply unit 14, the observation light is guided through a light guide (not shown) of the endoscope 18 and illuminates the body cavity. When the operator then turns on a main switch of the laser apparatus 18, the motor 29 is driven to rotate the chopper 25. The marker laser oscillator 24 then oscillates to generate a marker laser beam. The marker laser beam from the marker laser oscillator 24 alternately becomes incident on the reflecting mirror 23 and is reflected by the reflecting surface 28 of the chopper 25 in the direction perpendicular to the incident direction, according to the rotation of the chopper 25. The marker laser beam incident on the reflecting mirror 23 is focused by the focusing lens 22 through the operating laser oscillator 21 and is incident on the laser probe 16 of the endoscope 11. The marker laser beam emerging from the laser probe 16 is radiated on the wall of the body cavity. The operator can observe the radiated wall portion through an eyepiece 11a of the endoscope 11. The operator observes the flashing marker laser beam. The flashing frequency is determined by the rotational speed of the chopper 25 to be from several Hz to several tens of Hz, which allows proper observation with the naked eye. When the operator confirms the flashing of the marker laser beam and hence the portion of the body cavity to be radiated, he depresses a foot switch 19. The switching circuit 33 is then actuated. In this condition, the photosensor 31 receives the marker laser beam intermittently reflected by the reflecting surfaces 28 of the chopper 25 and produces a photosignal 31a with a waveform shown in FIG. 5. The photosignal 31a from the photosensor 31 is then converted to an integration signal 32a by the photosignal detector 32. When the integration signal 32a is supplied to the switching circuit 33, the switching circuit 33 causes the power source 34 to be ON. The power source 34 supplies a lighting current to the energizing lamp 35 to turn it on. The pumping light from the energizing lamp 35 excites the operating laser oscillator 21 to generate the operating laser beam. The operating laser beam is coaxially focused together with the marker laser beam by the focusing lens 22 onto the laser probe 16. The operating laser beam is radiated on the predetermined portion of the body cavity for treatment through the laser probe 16. In this case, since the marker laser beam flashes and is superposed on the operating laser beam, the operator can confirm the portion to be radiated with the operating laser beam and perform the proper treatment. When the operator releases the foot switch 19, the radiation of the operating laser beam is stopped. Only the marker laser beam flashes on the radiated portion.

As described above, since the marker laser beam flashes, the portion radiated by the operating laser beam can be easily confirmed even if the color of the radiated portion is similar to that of the marker laser beam. Further, only when the marker laser beam is emitted, the operating laser oscillator is driven. Therefore, an undesired portion of the body cavity will not be accidentally radiated by the operating laser beam, thus achieving safe treatment.

Figure 7:
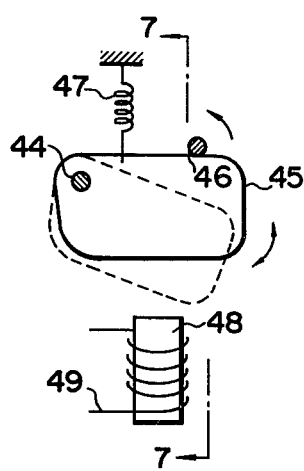
FIG. 7 is a side view of a chopper used in the laser apparatus shown in FIG. 6.
Figure 8:
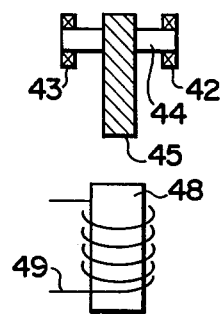
FIG. 8 is a sectional view of the chopper shown in FIG. 7.
Figure 6:
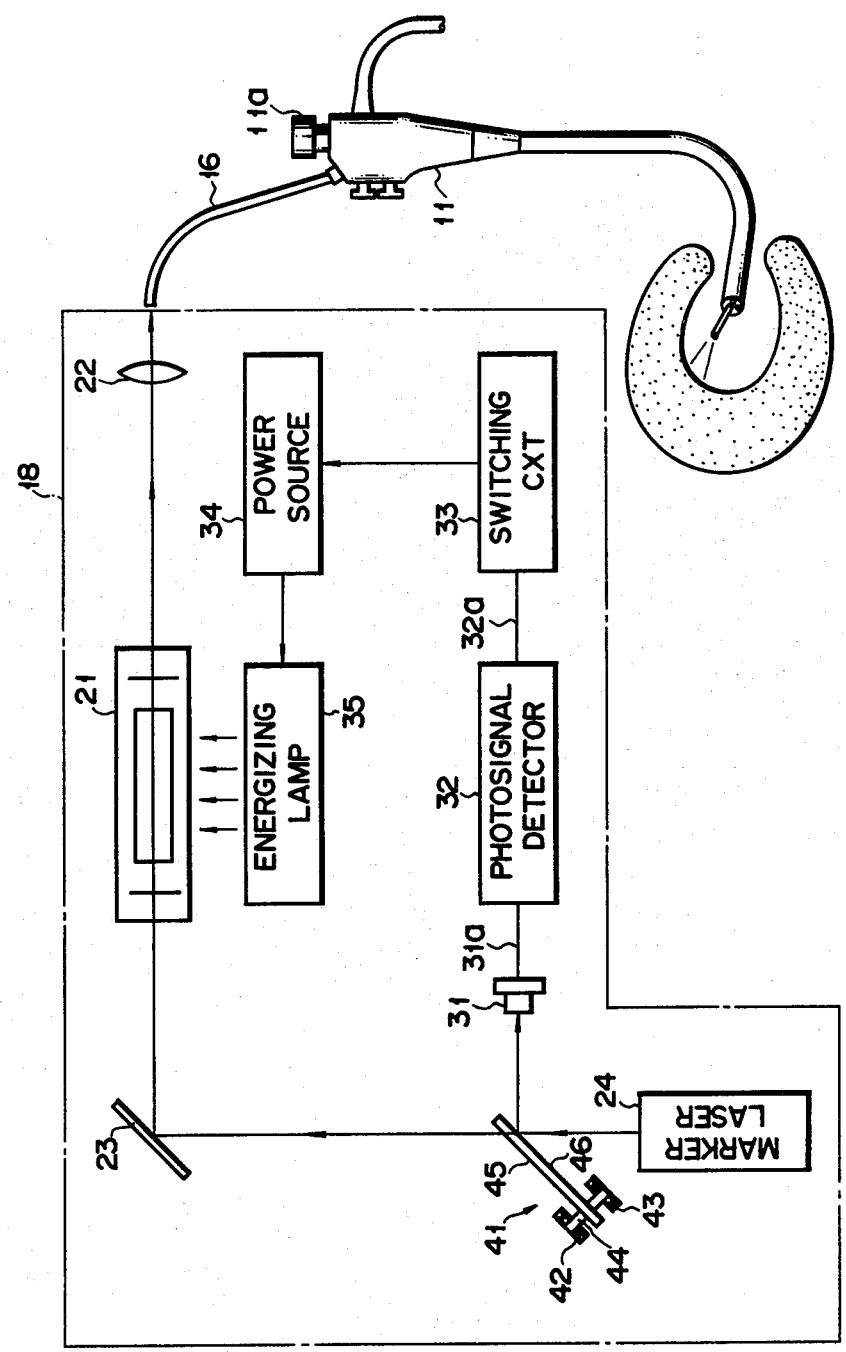
FIG. 6 is a schematic view of an endoscope system using a laser apparatus according to another embodiment of the present invention.

According to the laser apparatus shown in FIG. 6, a chopper 41 has a reflecting plate 45 which is free to pivot and which is mounted on a shaft 44 rotatably mounted on bearings 42 and 43. The reflecting plate 45 is inclined at, for example, 45° with respect to the marker laser oscillator 24 and the photosensor 31. A spring 47 is mounted on the upper portion of the reflecting plate 45, as shown in FIG. 7. The reflecting plate 45 abuts against a stopper 46 by the urging force of the spring 47. In this condition, the marker laser beam is reflected toward the photosensor 31. An electromagnet 48 is disposed below the reflecting plate 45, as shown in FIGS. 7 and 8. When an energizing current is supplied to a coil 49 of the electromagnet 48, the reflecting plate 45 is attracted downward by the magnetic force of the electromagnet 48 against the urging force of the spring 47. Thus, the marker laser beam is incident on the reflecting mirror 23. When a pulse current of several Hz to several tens of Hz is supplied to the coil 49, the reflecting plate 45 pivots. The marker laser beam flashes and is incident on the laser probe 16 and the photosensor 31. Therefore, in the same manner as in the first embodiment, the radiated portion can be properly confirmed. Any undesired portion of the body cavity will not be accidentally radiated by the operating laser beam without confirmation.

In summary, according to the present invention, since the marker laser beam is selectively and intermittently guided to the laser probe of the endoscope and to the operating laser oscillator control section by the chopper, the operator can properly confirm the portion to be radiated by the flashing of the marker laser beam. Further, only when the marker laser beam is generated, the operating laser beam is generated, thus achieving safe treatment of the desired portion of the body cavity with a laser beam.

What is claimed is:

1. A laser apparatus comprising:
   an operating laser oscillator for generating an operating laser beam;
   a marker laser oscillator for generating a visible marker laser beam;
   means for guiding the visible marker laser beam coaxially with the operating laser beam to a laser probe of an endoscope;
   chopping means for shielding and reflecting the visible marker laser beam from said marker laser oscillator in a predetermined direction at a predetermined frequency;
   marker laser beam detecting means for detecting the visible marker laser beam shielded and reflected by said chopping means and for generating a detection signal; and
   energizing means for driving said operating laser oscillator in response to the detection signal from said marker laser beam detecting means.

2. An apparatus according to claim 1, wherein said marker-laser beam chopping means comprises a chopper which is interposed between said marker laser oscillator and said guiding means, which rotates at a predetermined speed, and which has a plurality of vanes each having a reflecting surface inclined with respect to a travelling direction of the visible marker laser beam.

3. An apparatus according to claim 1, wherein said marker-laser beam chopping means comprises a chopper plate which is interposed between said marker laser oscillator and said guiding means, which has a reflecting surface inclined with respect to the travelling direction of the visible marker laser beam, and which shields the visible marker laser beams at a predetermined frequency by pivoting at the predetermined frequency.

4. An apparatus according to claim 1, 2 or 3, wherein the predetermined frequency is in a range of several Hz to several tens of Hz.

5. An apparatus according to claim 1, 2 or 3, wherein said guiding means comprises a reflecting mirror for guiding the visible marker laser beam along an optical axis of said operating laser oscillator.

6. An apparatus according to claim 1, 2 or 3, wherein said marker-laser beam detecting means comprises a photosensor for receiving the visible marker laser beam reflected by said chopping means to convert the visible marker laser beam to a photoelectric signal, and means for integrating the photoelectric signal to generate an integration signal as a detection signal.

7. An apparatus according to claim 1, 2 or 3, wherein said energizing means comprises an energizing lamp disposed in the vicinity of said operating laser oscillator, and means for turning on said energizing lamp in response to the detection signal from said marker laser beam detecting means.

8. An apparatus according to claim 1, 2 or 3, wherein said operating laser oscillator comprises a YAG laser oscillator.

9. An apparatus according to claim 1, 2 or 3, wherein said marker laser oscillator comprises a helium-neon laser oscillator.

* * * * *